| United States Patent [19] | [11] Patent Number: 5,075,483 |
| Odorisio et al. | [45] Date of Patent: Dec. 24, 1991 |

[54] SUBSTITUTED 1,3,2-BENZOXAZAPHOSPHOLIDINES AND STABILIZED COMPOSITIONS

[75] Inventors: Paul A. Odorisio, Edgewater, N.J.; Stephen D. Pastor; James L. Hyun, both of Danbury, Conn.

[73] Assignee: Ciba-Geigy Corporation, Ardsley, N.Y.

[21] Appl. No.: 572,749

[22] Filed: Aug. 23, 1990

[51] Int. Cl.⁵ ............................................. C07F 9/6584
[52] U.S. Cl. ...................................................... 558/81
[58] Field of Search ........................................... 558/81

[56] References Cited

U.S. PATENT DOCUMENTS

| 3,574,797 | 4/1971 | Hodan et al. | 558/76 |
| 3,632,690 | 1/1972 | Dever et al. | 558/76 |
| 3,773,711 | 11/1973 | Dever et al. | 558/76 |
| 3,796,684 | 3/1974 | Dever et al. | 558/76 |
| 3,831,178 | 5/1969 | Odorisio et al. | 558/76 |
| 4,751,319 | 6/1988 | Odorisio et al. | 558/76 |

OTHER PUBLICATIONS

Pastor et al., "J. Am. Chem. Soci.", Vol. 110, (1988) pp. 6547-6555.
Chem. Abst. 95, 98869l (1981).
Chem. Abst. 73, 35513d (1969).
Chem. Abst. 97, 163102b (1982).
Chem. Abst. 79, 137054w (1973).
Chem. Abst. 101, 171367h (1984).
Chem. Abst. 100, 85824c (1983).
Chem. Abst. 91, 39590w (1979).
Chem. Abst. 83, 9913w (1975).
Chem. Abst. 80, 83139c (1973).
Chem. Abst. 78, 43606e (1972).
Chem. Abst. 103, 215403q (1985).
Chem. Abst. 73, 14858e (1969).

*Primary Examiner*—Mary C. Lee
*Assistant Examiner*—Michael G. Ambrose
*Attorney, Agent, or Firm*—Luther A. R. Hall

[57] ABSTRACT

Substituted 1,3,2-benzoxazapholidines of formula I

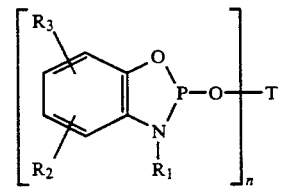

wherein $R_1$, $R_2$ and $R_3$ are independently hydrogen, alkyl, cycloalkyl, phenylalkyl or aryl, n is 1 to 4, and T is an n-valent aliphatic or aromatic hydrocarbon radical are effective in stabilizing organic materials against the deleterious effects of oxygen, heat and actinic radiation.

7 Claims, No Drawings

SUBSTITUTED 1,3,2-BENZOXAZAPHOLIDINES AND STABILIZED COMPOSITIONS

The present invention relates to novel substituted 1,3,2-benzoxazapholidines and their use as stabilizers for various organic materials subject to the deleterious effects of oxygen, heat or actinic radiation. The instant compounds provide both melt flow stabilization during polymer processing as well as good retention of polymer physical properties during long-term thermooxidative stress.

BACKGROUND OF THE INVENTION

U.S. Pat. Nos. 4,751,319; 4,812,501 and 4,831,178 describe aliphatic and aryl esters of 1,3,2-oxazapholidines as color improvers and process stabilizers for various polymer substrates. The compounds described in these patents lack the benzo ring of the instant compounds, but are superior to the prior art compounds in stabilization effectiveness. The effect of the benzo ring is not obvious. There are electronic effects upon the heteroatoms (i.e. reduction in basicity of the nitrogen atom), changes in conformation and reactivity, the O—C=C—N fragment must be planar and a change in hydrolytic stability.

U.S. Pat. Nos. 3,574,797 and 3,773,711 describe 2-phenoxy-4,5-dibenzo-1-oxa-3-thia-2-phospholanes as polymer stabilizers. The instant compounds are structurally clearly different from the material disclosed in these patents.

U.S. Pat. Nos. 3,632,690 and 3,796,684 describe substituted 4,5-benzo-1,3,2-dioxapholanes as polymer stabilizers. The instant compounds are structurally clearly distinguished from the compounds disclosed in these patents.

East German 146,464 and French 1,573,919 disclose 1H-1,3,2-benzodiazapolyphospholes as polymer stabilizers and antibacterials respectively. The instant compounds are clearly quite different from the compounds disclosed in these references.

There are a number of academic studies carried on in the Soviet Union on the preparation and physical properties of the 2-methyl, 2-ethyl, 2-isopropyl, butyl and phenyl esters of 4,5-benzo-1,3,2-oxazapholanes. These references are Zh. Obshch. Khim, 52, 1302 (1982); ibid, 43, 1860 (1973), ibid, 54, 1283 (1984); ibid, 53, 2468 (1983); ibid, 49, 955 (1979); ibid, 45, 266 (1975); ibid, 43, 2619 (1973); ibid, 42, 1901 (1972); and ibid, 55, 1184 (1985); and Chem. Abst. 73, 14858e (Soviet Union 245,101).

The instant compounds are structurally distinguished from each of the compounds disclosed in these prior art references and exhibit surprising stabilizing properties which further distinguish them from the prior art. This is manifested in the superior processing stabilization of polymeric substrates and in the maintenance of physical properties of polymeric substrates exposed to long-term thermooxidative stress.

OBJECTS OF THE INVENTION

One object of the instant invention is to provide new substituted 1,3,2-benzoxazapholidines which have stabilization properties for organic materials subject to oxidative, thermal and/or actinic degradation.

Another object of the invention is to provide stabilized compositions containing the substituted 1,3,2-benzoxazapholidines of this invention.

DETAILED DISCLOSURE

The instant invention pertains to novel substituted 1,3,2-benzoxazapholidines of formula I

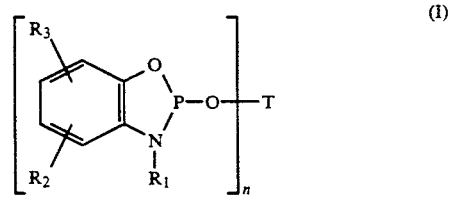

wherein n is an integer from 1 to 4, $R_1$, $R_2$ and $R_3$ are independently hydrogen, alkyl of 1 to 18 carbon atoms, cycloalkyl of 5 to 12 carbon atoms, phenylalkyl of 7 to 15 carbon atoms or said phenylalkyl substituted on the phenyl ring by alkyl of 1 to 12 carbon atoms, aryl of 6 to 10 carbon atoms or said aryl substituted by one or two alkyl of 1 to 12 carbon atoms, and T is an n-valent aliphatic or aromatic radical, when n is 1, T is alkyl of 8 to 20 carbon atoms, said alkyl interrupted by one to nine —O—, —S—, —SO—, —SO$_2$—, —CO—, —COO—, —CONR$_4$— or —NR$_5$— or mixtures thereof where $R_4$ and $R_5$ independently have the same definitions as $R_1$, or T is aryl of 6 to 10 carbon atoms which is substituted by one, two or three alkyl of 1 to 12 carbon atoms or said aryl substituted by —(CH$_2$)$_k$—COOR$_6$ where k is 0, 1, or 2, and $R_6$ is alkyl of 1 to 20 carbon atoms, or T is phenylalkyl of 7 to 15 carbon atoms or where the alkyl is interrupted by one or two —O—, —S—, —SO— or —SO$_2$—, or where the phenyl ring is substituted by one, two or three alkyl of 1 to 12 carbon atoms, when n is 2, T is a straight or branched chain alkylene of 2 to 31 carbon atoms, said alkylene interrupted by one to seven —O—, —S—, —SO— or —SO$_2$— moieties, cycloalkylene of 6 to 12 carbon atoms, phenylene, phenylene substituted by one to four alkyl groups of 1 to 4 carbon atoms, xylylene, or phenylene-E-phenylene where E is a direct bond, methylene, alkylidene of 2 to 8 carbon atoms, —O—, —S—, —SO—, —SO$_2$—, —CO— or —NR$_5$, when n is 3, T is alkanetriyl of 3 to 6 carbon atoms or benzenetriyl, and when n is 4, T is alkanetetrayl of 4 to 6 carbon atoms.

Preferably, $R_1$, $R_2$ and $R_3$ independently are hydrogen or alkyl of 1 to 8 carbon atoms; most preferably $R_2$ and $R_3$ are independently hydrogen or methyl, and $R_1$ is hydrogen or alkyl of 1 to 8 carbon atoms.

Preferably, n is 1 and T is the monovalent radical of formula II

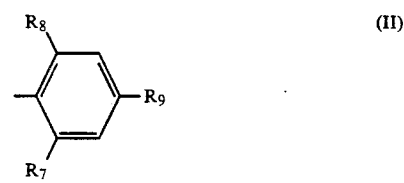

where $R_7$, $R_8$ and $R_9$ are independently hydrogen, alkyl of 1 to 18 carbon atoms, cycloalkyl of 5 to 7 carbon atoms or phenylalkyl of 7 to 9 carbon atoms, or $R_9$ is also —$(CH_2)_k$—$COOR_6$ where k is 0, 1 or 2 and $R_6$ is alkyl of 1 to 20 carbon atoms.

Most preferably, n is 1 and T is formula II where $R_7$ is hydrogen or alkyl of 1 to 8 carbon atoms, $R_8$ is alkyl of 3 to 8 carbon atoms and $R_9$ is alkyl of 3 to 8 carbon atoms or —$CH_2CH_2COOR_6$ where $R_6$ is alkyl of 1 to 18 carbon atoms.

The instant invention also pertains to stabilized compositions containing an effective stabilizing amount of a compound of formula I defined as above where additionally T is also alkyl of 1 to 20 carbon atoms or aryl of 6 to 10 carbon atoms.

The compounds of this invention are conveniently prepared by the reaction of an ortho-aminophenol with an alkyl phosphorodichloridite or an aryl phosphorodichloridite. The ortho-aminophenols are largely items of commerce while the phosphorodichloridites are conveniently prepared by reaction of an alcohol or phenol with phosphorus trichloride.

The instant compounds are also prepared by the reaction of an ortho-aminophenol with phosphorus trichloride to form the substituted benzoxazaphospholidine-2-chloro intermediate which is then reacted with an alcohol, glycol or phenol to give the instant compounds in the presence of an acid acceptor such as triethylamine.

When any of $R_1$ to $R_9$ or T is alkyl, such alkyl groups are, for example, methyl, ethyl, isopropyl, n-butyl, tert-butyl, tert-amyl, 2-ethylhexyl, n-octyl, lauryl, n-octadecyl and eicosyl; when said radicals are cycloalkyl, they are, for example cyclopentyl, cyclohexyl, cyclooctyl and cyclododecyl; when said radicals are phenylalkyl, they are, for example, benzyl, phenethyl, α-methylbenzyl and α,α-dimethylbenzyl; when said radicals are aryl, they are, for example, phenyl, naphthyl, or when substituted by alkyl are, for example, tolyl and xylyl; when said radicals are alkyl interrupted by —O—, they are for example, 3-oxaamyl and 3,6-dioxaoctyl; when T is alkylene, said alkylene interrupted by —O— or cycloalkylene, T is, for example, ethylene, trimethylene, tetramethylene, hexamethylene, 2,2-dimethylpropane-1,3-diyl, cyclohexylene, 3-oxapentamethylene and 3,6-dioxaoctamethylene; when T is alkanetriyl, it is, for example, glyceryl, trimethylyl propane; and when T is alkanetetrayl, T is, for example, pentaerythrityl or 1,2,3,4-butanetetrayl.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber; and lubricating oils.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopenteneor norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from α,β-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha$,$\alpha$-dimethylbenzyl)-4-nonylphenol]
2,2'-methylene-bis-(4,6-di-tert-butylphenol)
2,2'-ethylidene-bis-(4,6-di-tert-butylphenol)

2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl, 5-chloro-3'-tert-butyl-5'-methyl-, 3'-sec-butyl-5'-tert-butyl, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β, β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxy-ethoxy)-phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)-benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)-butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylene-bis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl] 1,2,3,4-butanetetracarboxylate, mixed [1,2,2,6,6- pentamethylpiperidin-4-yl/$\beta,\beta,\beta',\beta'$-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate) and 4,4'-ethylenebis(2,2,6,6-tetramethylpiperazin-3-one).

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine) or N,N',N'',N'''-tetrakis[(4,6-bis(butyl-(2,2,6,6-tetramethyl-piperidin-4-yl)amino)-s-triazine-2-yl]-1,10-diamino-4,7-diazadecane.

The following examples are presented for the purpose of illustration only and are not to be construed to limit the nature or scope of the instant invention in any manner whatsoever.

EXAMPLE 1

2-[2,6-Di-tert-butyl-4-(2-(n-octadecyloxycarbonyl)ethyl)-phenoxy]-1,3,2-benzoxazaphospholidine Into a cooled solution of 29.8 g (50 mmol) of 2,6-di-tert-butyl-4-[2-(n-octadecyloxycarbonyl)ethyl]-phenyl phosphorodichloridite in 100 ml of methylene chloride at dry ice/acetone temperature is added a solution of 5.46 g (50 mmol) of 2-aminophenol and 13.95 ml (100 mmol) of triethylamine in 25 ml of methylene chloride. After the addition is complete, the mixture is warmed to room temperature with continual stirring. After 16 hours, the reaction mixture is concentrated under reduced pressure, mixed with 50 ml of toluene and filtered to remove insoluble solids. The filtrate is reconcentrated, dissolved in hexane and treated with decolorizing charcoal. The resultant mixture is clarified and the filtrate concentrated under reduced pressure to give 27.6 g of the title compound as a white solid melting at 58°-65° C.

$^{31}$P NMR($C_6D_6$)133.4 ppm.

Analysis: Calcd for $C_{41}H_{66}NO_4P$: C, 73.7; H, 10.0; N, 2.1. Found: C, 73.7; H, 9.9; N, 1.9.

EXAMPLE 2

2-(2,4,6-Tri-tert-butylphenoxy)-1,3,2-benzoxazaphospholidine

Using the general procedure of Example 1, 12.0 g (33 mmol) of 2,4,6-tri-tert-butylphenyl phosphorodichloridite, 3.6 g (33 mmol) of 2-aminophenol, 9.3 ml (66 mmol) of triethylamine and 75 ml of methylene chloride are reacted to give 3.5 g of the title compound as an off-white solid.

$^{31}$P NMR 132.2 ($C_6D_6$) 132.2 ppm.

Analysis: Calcd for $C_{24}H_{34}NO_2P$: C, 72.2; H, 8.6; N, 3.5. Found: C, 71.9; H, 8.7; N, 3.4.

EXAMPLE 3

Process Stabilization of Polypropylene at 536° F. (280° C.)

The base formulation comprises unstabilized, new technology polypropylene (Profax 6501, Himont) containing 0.1% by weight of calcium stearate. The test stabilizer is solvent blended onto the polypropylene from a solution in methylene chloride. After removal of the solvent by evaporation under reduced pressure, the stabilized resin formulation is extruded at 80 rpm from a 1 inch (2.54 cm) diameter extruder at 536° F. (280° C.) with a residence time of 45 seconds.

After each of the first and fifth extrusions, the melt flow rate (in grams/10 minutes) is determined by ASTM method D1238 on the pellets obtained from the extruder. The nominal melt flow rate for Profax 6501 with 0.5% by weight of BHT* is 3.1 g/10 min. The results are given in the table below.

*BHT is 2,6-di-tert-butyl-4-methylphenol

| Additive* | Concentration (% by weight) | Melt Flow Rate after Extrusion 1 | 5 |
|---|---|---|---|
| None | — | 10.7 | >30 |
| AO A | 0.1 | 4.3 | 12.7 |
| Compound of Example 1 | 0.1 | 2.6 | 5.7 |
| AO A plus Example 1 Compound | 0.1 0.05 | 2.7 | 6.1 |

*AO A is neopentanetetrayl tetrakis-(3,5-di-tert-butyl-4-hydroxyhydrocinnamate).

The instant compound of Example 1 is more effective than the phenolic antioxidant as a process stabilizer for polypropylene.

EXAMPLE 4

Oxygen Uptake Screening of Antioxidants

This example illustrates the effectiveness of the instant compounds as radical initiated oxidation inhibitors.

A chlorobenzene solution (20 ml), 1.0 molar in tetralin and $2 \times 10^{-3}$ molar in test compound, is charged into a 100 ml reaction flask equipped with a ball-joint side arm. The assembly is then connected to a pressure transducer which allows automatic monitoring of pressure changes within the sealed flask as oxygen is consumed. The system is partially evacuated and flushed with pure oxygen five times, sealed and placed in an oil bath at 60° C., and stirred with a magnetic stirrer bar. After thermal equilibration (15 minutes), the system is vented to atmospheric pressure, 98.5 mg, (0.60 mmol, $3.0 \times 10^{-2}$ molar) of 2,2'-azobis(isobutyronitrile), AIBN, is added, and the system resealed. The pressure in the sealed system is monitored continuously as oxygen is being consumed (total gas volume is approximately 95 ml).

By measuring oxygen consumption as a function of time in an AIBN-initiated oxidation, the length of the induction period and the time required to absorb 1.0 mmol of oxygen are determined. The results are given in the table below.

| Additive* | Induction Period (in hours) | Time to 1.0 mmol of Oxygen Uptake (in hours) |
|---|---|---|
| None | 0 | 3.7 |
| AO B | 3.0 | 6.6 |
| Compound of Example 1 | 5.6 | 12.0 |

*AO B is 2,6-di-tert-butyl-4-methylphenol.

The instant compound exhibits a much longer induction period and much longer time for uptake of oxygen than the prior art phenolic antioxidant.

EXAMPLE 5

When, following the general procedure of Example 3, a hindered amine compound is substituted for the phenolic antioxidant, a combination of said hindered amine compound plus instant compound provides polypropylene with effective stabilization against thermal oxidative degradation.

What is claimed is:

1. A compound of formula I

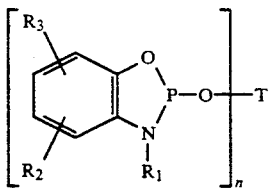

wherein n is an integer from 1 to 4, $R_1$, $R_2$ and $R_3$ are independently hydrogen, alkyl of 1 to 18 carbon atoms, cycloalkyl of 5 to 12 carbon atoms, phenylalkyl of 7 to 15 carbon atoms or said phenylalkyl substituted on the phenyl ring by alkyl of 1 to 12 carbon atoms, aryl of 6 to 10 carbon atoms or said aryl substituted by one or two alkyl of 1 to 12 carbon atoms, and T is an n-valent aliphatic or aromatic radical, when n is 1, T is alkyl of 8 to 20 carbon atoms, said alkyl interrupted by one to nine —O—, —S—, —SO— —SO$_2$—, —CO—, —COO—, —CONR$_4$— or —NR$_5$— or mixtures thereof where $R_4$ and $R_5$ independently have the same definitions as $R_1$, or T is aryl of 6 to 10 carbon atoms which is substituted by one, two or three alkyl of 1 to 12 carbon atoms or said aryl substituted by —(CH$_2$)$_k$—COOR$_6$ where k is 0, 1, or 2, and $R_6$ is alkyl of 1 to 20 carbon atoms, or T is phenylalkyl of 7 to 15 carbon atoms or where the alkyl is interrupted by one or two —O—, —S—, —SO— or —SO$_2$—, or where the phenyl ring is substituted by one, two or three alkyl of 1 to 12 carbon atoms, when n is 2, T is a straight or branched chain alkylene of 2 to 31 carbon atoms, said alkylene interrupted by one to seven —O—, —S—, —SO— or —SO$_2$— moieties, cycloalkylene of 6 to 12 carbon atoms, phenylene, phenylene substituted by one to four alkyl groups of 1 to 4 carbon atoms, xylylene, or phenylene-E-phenylene where E is a direct bond, methylene, alkylidene of 2 to 8 carbon atoms, —O—, —S—, —SO—, —SO$_2$—, —CO— or —NR$_5$, when n is 3, T is alkanetriyl of 3 to 6 carbon atoms or benzenetriyl, and when n is 4, T is alkanetetrayl of 4 to 6 carbon atoms.

2. A compound according to claim 1 where $R_1$, $R_2$ and $R_3$ independently are hydrogen or alkyl of 1 to 8 carbon atoms.

3. A compound according to claim 2 where $R_2$ and $R_3$ are independently hydrogen or methyl, and $R_1$ is hydrogen or alkyl of 1 to 8 carbon atoms.

4. A compound according to claim 1 where n is 1 and T is the monovalent radical of formula II

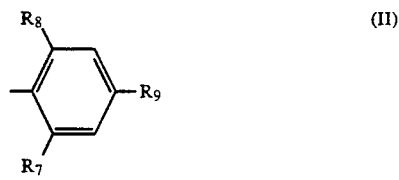

where $R_7$, $R_8$ and $R_9$ are independently hydrogen, alkyl of 1 to 18 carbon atoms, cycloalkyl of 5 to 7 carbon atoms or phenylalkyl of 7 to 9 carbon atoms, or $R_9$ is also —(CH$_2$)$_k$—COOR$_6$ where k is 0, 1 or 2 and $R_6$ is alkyl of 1 to 20 carbon atoms.

5. A compound according to claim 4 where n is 1 and T is formula II where $R_7$ is hydrogen or alkyl of 1 to 8 carbon atoms, $R_8$ is alkyl of 3 to 8 carbon atoms and $R_9$ is alkyl of 3 to 8 carbon atoms or —CH$_2$CH$_2$COOR$_6$ where $R_6$ is alkyl of 1 to 18 carbon atoms.

6. The compound according to claim 1 which is 2-[2,6-di-tert-butyl-4-(2-(n-octadecyloxycarbonyl)ethyl)-phenoxy]-1,3,2-benzoxazaphospholidine.

7. The compound according to claim 1 which is 2-(2,4,6-tri-tert-butylphenoxy)-1,3,2-benzoxazaphospholidine.

* * * * *